United States Patent
Rainin et al.

(10) Patent No.: US 6,568,288 B2
(45) Date of Patent: May 27, 2003

(54) PIPETTE WITH IMPROVED PIPETTE TIP AND MOUNTING SHAFT

(75) Inventors: Kenneth Rainin, Piedmont, CA (US); James S. Petrek, Danville, CA (US)

(73) Assignee: Rainin Instrument, LLC, Oakland, CA (US)

( * ) Notice: Subject to any disclaimer, the term of this patent is extended or adjusted under 35 U.S.C. 154(b) by 0 days.

(21) Appl. No.: 09/895,745

(22) Filed: Jun. 29, 2001

(65) Prior Publication Data

US 2003/0000319 A1 Jan. 2, 2003

(51) Int. Cl.$^7$ ................................................. G01N 1/00
(52) U.S. Cl. .................................................... 73/864.16
(58) Field of Search ............ 73/864.14, 864.16–864.18; 422/100; 436/180

(56) References Cited

U.S. PATENT DOCUMENTS

| | | | | |
|---|---|---|---|---|
| 3,786,683 A | * | 1/1974 | Berman et al. | 73/864.14 |
| 4,748,859 A | * | 6/1988 | Magnussen, Jr. et al. | 73/864.14 |
| 4,863,695 A | * | 9/1989 | Fullemann | 73/864.14 |
| 5,232,669 A | * | 8/1993 | Pardinas | 73/864.14 |

* cited by examiner

Primary Examiner—Robert Raevis
(74) Attorney, Agent, or Firm—Robert R. Meads

(57) ABSTRACT

An air displacement pipette having axially spaced annular sealing and substantially cylindrical lateral support zones and regions on the pipette's mounting shaft and tip, respectively, in combination with means for insuring uniform depth of mounting shaft penetration into the pipette tip to maintain uniform tip interference with the mounting shaft as successive tips are mounted on and ejected from the mounting shaft whereby the pipette tip is easily and firmly mountable on and easily ejectable from the pipette tip mounting shaft by the application of axial mounting and ejection forces of about two pounds and one pound, respectively.

14 Claims, 4 Drawing Sheets

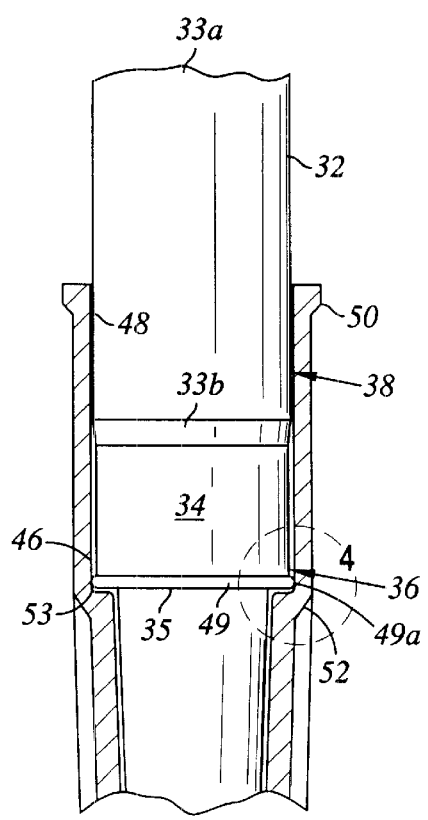
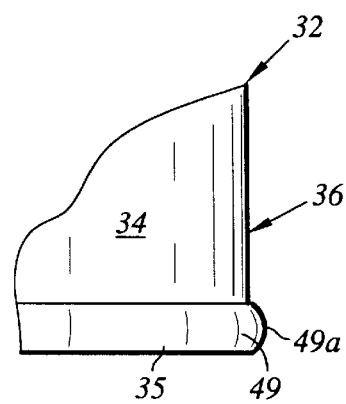
Fig. 3
Fig. 4

PIPETTE WITH IMPROVED PIPETTE TIP AND MOUNTING SHAFT

BACKGROUND OF THE INVENTION

The present invention relates to improvements in pipettes and, more particularly, to air displacement pipettes including a novel mounting shaft and a unique pipette tip tailored to the mounting shaft such that the tip is easily insertable by a pipette user onto the shaft to a fluid tight position in which the tip is secured against undesired lateral rocking on or displacement from the shaft and, after use, is easily ejectable from the shaft by the pipette user; such tip insertion and ejection requiring the pipette user to only exert axial tip insertion and ejection forces of about one pound or less thereby substantially reducing the risk of repetitive motion injury to the pipette user.

The use of pipette devices for the transfer and dispensing of precise quantities of fluids in analytical systems is well known as is the use of disposable tip members for such pipettes. Disposable tips accommodate the serial use of such pipette devices in the transfer of different fluids without carryover or contamination.

Generally speaking, disposable pipette tips are formed of a plastic material and are of a hollow, elongated, generally conical shape with an open proximal end for receiving and releasably mating with the distal end of an elongated generally conical pipette tip mounting shaft of a pipette device. Ideally, the disposable tip should slide easily onto the mounting shaft to an axial position adjacent a lower end of a tip ejection mechanism of the pipette device. Thus located, the pipette tip should be laterally stable on the shaft, free from external rocking relative to the shaft (as during "touching off"), and should form a fluid tight annular seal with the mounting shaft. Then, when it is desired to replace the tip with a new tip, the pipette tip should be easily removed from the mounting shaft by operation of the tip ejection mechanism.

To meet the desired sealing criteria for disposable pipette tips on pipette tip mounting shafts, the inner surface and side walls of the proximal portions of most pipette tips are axially tapered at a one to one and a half degree greater angle than the distal end of the pipette tip mounting shaft and form an axially elongated frusto-conical annular sealing band. The sealing band is dimensioned to stretch outwardly ("hoop stretch") as the distal end of the elongated generally conical pipette tip mounting shaft is forced into the proximal end of the tip to firmly seat the tip on the shaft and to create an axially elongated annular fluid tight seal between the sealing band and the mounting shaft. Other pipette tips, such as those described in U.S. Pat. Nos. 4,748,859 and 4,824,641, include a plurality of axially spaced compressible annular sealing rings on an inner surface of the proximal end portion of such tips. The rings create multiple axially spaced fluid tight annular seals between the outer surface of the pipette tip mounting shaft and the inner surface of the proximal end portion of the tip which by virtue of the axially spaced rings is laterally stabilized against undesired rocking on the shaft during touching off.

Usually, in mounting a pipette tip on a mounting shaft of a pipette, a user, exerting a downward force of between eight and fifteen pounds, drives the mounting shaft axially into the tip a distance which to the user seems sufficient to create (i) a fluid tight seal between the tip and (ii) the desired lateral stability for the tip on the shaft. On occasion, in a mistaken attempt to improve the lateral stability of a pipette tip on a mounting shaft, a user will exert a downward insertion force (e.g. eighteen to twenty-five pounds) on the shaft sufficient to axially drive the tip on the shaft until an upper surface of the tip engages or is wedged into the ejector arm or cone of the tip ejector mechanism of the pipette. The contact between a lower surface of the tip ejector arm or cone and the upper surface of the tip, however, only provides a minimal resistance to rocking of the tip on the shaft and hence only results in a minimal increase in the lateral stability of the tip on the shaft. Further, since most pipette tips are formed of a relatively rigid plastic material, the annular stretching of the pipette tip required to accommodate movement of the tip onto the shaft particularly to a point where it engages the lower surface of the tip ejector or cone is difficult to achieve. In fact, the axial forces which must be exerted on a conventional pipette to achieve such a positioning of the tip on the pipette tip mounting shaft frequently exceed twelve and may be as great as twenty pounds, which is difficult for many pipette tip users to generate. Of course, with most pipette tip designs, the greater the axial force exerted in seating a pipette tip on a pipette mounting shaft, the greater the force required to eject the tip from the mounting shaft. Thus, while the insertion of a pipette tip onto a mounting shaft until it reaches a position against a lower surface of a pipette tip ejector mechanism provides a minimum increase in the lateral stability of the tip on the shaft, it works against the design criteria for disposable pipette tips that they be easily removable from the shaft when it is desired to replace the tip.

In fact, the design criteria for disposable pipette tips that they be stably mountable on and form a fluid tight seal with a pipette mounting shaft is more easily achieved than the design criteria that disposable pipette tips slide easily onto a pipette tip mounting shaft to an axial location forming a fluid tight seal and then be easily removable from the mounting shaft when it is desired to replace the tip.

In these regards, the pipette tip mounting shafts of devices for pipetting volumes of liquid in different ranges have different external shape. For example, the distal end of standard pipette tip mounting shafts of pipettes for pipetting liquids in volumes greater than 500 microliters (large volume pipettes) commonly have a downward and inward axial taper of about one and one half to two and one half degrees per side from the longitudinal axis of the mounting shaft. On the other hand, the distal end of the mounting shafts of moderate to relatively small volume pipette devices (250 microliters and less) commonly have a downward and inward axial taper of about two to five degrees per side from the longitudinal axis of the mounting shaft so that the nose of the shaft will hit the inner wall of the pipette tip and cause hoop stretching thereof before the side of the shaft engages the inner wall of the tip. Therefore, while the design criteria that a large volume pipette tip be easily mountable on and easily removable from the mounting shaft of a large volume pipette device may be achieved by including a proximal end portion having a side wall of reduced wall thickness as in the large volume pipette tip described in U.S. Pat. No. 5,779,984, issued Jul. 14, 1998, such a thin wall design will not result in a pipette tip that satisfies the easy mount and ejection design criteria of moderate and small volume pipette tips which must firmly mount on pipette tip mounting shafts having an inward taper of two degrees and above. The same is true of the pipette tip design disclosed in U.S. Pat. No. 4,072,330 which includes a broad frusto-conical sealing region having a thin side wall for mating with axially broad conically tapered or spherically convex collars extending outward and spaced some distance from distal ends of associated pipette tip mounting shafts.

As previously stated, standard small and moderate volume pipette tips include a frusto-conical annular sealing band or inner surface for engaging and sealing with the tapered distal end of a pipette tip mounting shaft. The angle of taper of the sealing surface usually approximates (e.g. one and one-half degrees greater than) that of the mounting shaft (e.g. two to five degrees). Thinning the side wall of the standard small and moderate volume pipette tips in the region of such a sealing band does little to reduce the mounting and ejection forces required to move such a tip to a sealing location and then eject the pipette tip from the mounting shaft. In forming the desired annular seal, the frusto-conical annular region is required to stretch like a hoop (hoop stretch) outwardly normal to the mating sloping surface of the pipette tip mounting shaft. Large reactive forces in the tip material resist such hoop stretching and require the exertion of large axial forces (eg. ten or more pounds) on the tip in order to mount the tip on the mounting shaft and create the necessary annular fluid tight seal. Such reactive forces increase as the tip is driven toward the tip ejection mechanism of the associated pipette device.

Further, disposable pipette tips are commonly mounted and stored in sterilizable racks. Such racks commonly include a support tray having an array of holes for receiving distal ends of pipette tips to vertically orient the pipette tips in a spaced rectilinear pattern with open proximal ends of the tips exposed to receive the mounting shafts of a pipette device onto which the pipette tips are to be mounted. For example, to mount the disposable pipette tips contained in a tip rack on the shafts of a multi-channel pipette, the pipette device is placed over the rack with its several mounting shafts aligned with the open proximal ends of an aligned series of the pipette tips. After a slight initial insertion of the mounting shafts into the open proximal ends of the aligned pipette tips, a relatively large downward force is exerted on the pipette device to drive the mounting shafts into the tip members. The pipette tips are thus very firmly seated on the mounting shafts and are lifted from the rack with upward movement of the multi-channel pipette. Unfortunately, in practice, such multiple pipette tip mounting procedures often result in some of the pipette tips being mounted at different axial locations on some of the mounting shafts. In an attempt to eliminate such non-uniform mounting of pipette tips on the several channels of a multi channel pipette, users often rock the pipette as the mounting shafts are driven by axial forces approximating 12 to 15 pound per channel into the tips supported by a pipette tip rack to drive the tips toward the lower surface of the tip ejector mechanism of the pipette. Also, it is frequently necessary to hand tighten each pipette tip on its associated mounting shaft to prevent undesired fluid leakage from the tips.

Moreover, the more firmly a tip is mounted or wedged on the mounting shaft of the pipette device, the greater the axial force which a pipette user must generate by thumb and hand action to eject the tip from the shaft when a tip replacement is desired. In practice, it is not uncommon for axial forces approximating twenty to twenty-five pounds to be generated by the pipette users thumb and hand in driving pipette tips from the mounting shafts of a multi-channel pipette. Over several and repeated ejection operations, particularly with multi-channel pipettes, the thumb and hand of the user become physically stressed often resulting in repetitive stress injury to the thumb and hand and in extreme cases, carpal tunnel syndrome.

Still further, standard pipette tips as well as those illustrated in U.S. Pat. No. 4,072,330 depend solely upon the sealing region of the pipette tip to both create the annular fluid tight seal and to provide the stable lateral mounting of the tip to the shaft sufficient to resist rocking as during touching off. The structure of such pipette tips do not provide such lateral mounting stability.

In an effort to improve lateral stability and retention of pipette tips on the mounting shafts of some pipettes, some manufacturers include O-rings on and encircling the tip mounting shafts of their pipettes. For example, the Brinkmann Instrument Co. indicates for its Transferpipette 8/12 that such O-rings ensure that all tips stay firmly mounted during use. However, there is a rapid wearing of such O-rings with repeated insertion of the associated mounting shafts into and ejection of pipette tips from such shafts. With such wear, the tips no longer stay firmly mounted during use and wear particles from the O-rings can contaminate fluid samples handled by the associated pipettes.

In an effort to reduce the hand and finger forces which a pipette user must generate to eject a tip from the mounting shaft of a pipette, other pipette manufacturers such as LabSystems have developed and include in some of their pipettes rack and gear mechanisms for amplifying the user generated forces to eject pipette tips from their mounting shafts. Unfortunately, such mechanisms are costly, add undesired size and weight to the pipettes and only achieve a force reduction of about 2 to 1.

More recently, to meet the previously described ideal characteristics and criteria for a pipette tip, there has been developed an improved plastic pipette tip which is mountable on and ejectable from a standard pipette mounting shaft of an air displacement pipette by application of an axial mounting force of less than six pounds and an axial ejection force as small as three pounds. The improved pipette tip is described in the U.S. Pat. No. 6,197,259, entitled "Easy Eject Pipette Tip", issued Mar. 6, 2001. As there described, to meet the mountability and ease of ejection criteria for disposable pipette tips, the improved pipette tip, hereinafter referred to as the "Soft Seal" tip, includes an open tubular proximal end portion comprising an enlarged frusto-conical open top tapering downwardly and inwardly to join at an annular sealing region to a hollow substantially cylindrical mid-portion of the pipette tip. The open top has an inner diameter sufficient to axially receive the distal end of a standard pipette tip mounting shaft. The annular sealing region is formed by the transition or line of connection of the frusto-conical open top to the mid-portion of the pipette and includes an annular sidewall having a thickness in a range of 0.20 to 0.50 mm. The mid-portion has an inner diameter at the sealing region which is less than the diameter of the pipette mounting shaft, a thin resilient annular side wall having a thickness in a range of 0.20 to 0.50 mm and an axial length in a range of 0.25 to 0.65 cm. Thus, while the distal end of the mounting shaft fits into the enlarged open end of the pipette tip, the frusto-conical outer surface of the mounting shaft engages the inner surface of the sealing region at the bottom of the open top of the pipette tip to stretch the annular sealing region or line radially outward as the mounting shaft is inserted into the proximal portion, thereby creating a fluid tight seal between the sealing zone and the sealing region. In addition to the proximal portion, the improved pipette tip includes a tubular distal portion extending from the mid-portion and terminating in a relatively narrow distal end opening for passing fluid into and from the tip upon operation of the pipette device. Finally, the improved pipette tip preferably includes lateral stabilizing means on its inner surface adjacent the sealing region for engaging the outer surface of the mounting shaft as it is inserted into the proximal portion to laterally stabilize the tip on the shaft. Such lateral stabilizing means preferably comprises at least three circumferentially spaced contacts extending inwardly from the inner surface of the proximal portion of the tip adjacent the sealing region for engaging the outer surface of the mounting shaft as it is inserted into the proximal portion to laterally stabilize the tip on the shaft. In this regard, the diametric spacing of the contacts is such that the contacts lightly engage and allow the distal end of the shaft to pass with no hoop stretching of the sidewalls from which the contacts extend. In this manner, the contacts combine with the sealing region to provide lateral support for the pipette tip on the mounting shaft and prevent the pipette tip from moving laterally when lateral external forces are exerted on the distal portion of the tip as during touching off.

While the "Soft Seal" pipette tip represented a substantial improvement over standard pipette tips with respect to the pipette tip mounting and ejection forces; the more recently developed "LTS" pipette tip and pipette tip mounting shaft system described in U.S. Pat. No. 6,168,761, reduces the risk of repetitive motion injuries to pipette users and minimizes pipette tip mounting and ejection forces to a degree previously thought to be unattainable. Specifically, the LTS system meets the heretofore unattainable ideal criteria that disposable plastic pipette tips (i) be easily mountable on a pipette tip mounting shaft to form a fluid tight connection with the shaft which is so secure that the tip will not rock laterally on or accidentally dislodge from the shaft during normal pipette use and (ii) then be easily ejectable from the mounting shaft by application of minimal axial mounting and ejection forces, e.g. forces approaching one pound or less. To achieve this, the LTS system incorporates in an air displacement pipette the concept of axially spaced annular sealing and substantially cylindrical lateral support zones and regions on the pipette's mounting shaft and tip, respectively. Preferably, the annular sealing region on the pipette tip comprises an annular sealing surface inward of a sidewall of the pipette tip which in the sealing region is sufficiently thin that the sealing region will expand slightly and form an interference fit and air tight seal between the sealing surface and the sealing zone on the mounting shaft when the sealing zone penetrates the sealing region. Further, the LTS system provides means for insuring uniform depth of mounting shaft penetration into the pipette tip to maintain uniform tip interference with the mounting shaft as successive tips are mounted on and ejected from the mounting shaft.

In particular, the LTS system incorporates a combination of a pipette tip mounting shaft and pipette tip in an air displacement pipette wherein the mounting shaft comprises an axially elongated body including a distal end and annular or substantially cylindrical and axially spaced outer surface regions defining an annular sealing zone and an annular lateral support zone. The pipette tip of the LTS system is an elongated tube comprising an open proximal end, an open conical distal end and annular or substantially cylindrical and axially spaced inner surface regions defining an annular sealing region and an annular lateral support region. The outer diameter of the annular sealing zone on the mounting shaft is slightly greater than the inner diameter of the annular sealing region on the pipette tip and the sidewall of the tip in the area of the annular sealing region is sufficiently thin that the annular sealing region expands slightly to form an interference fit and air tight seal between the mounting shaft and the pipette tip when the sealing zone penetrates the sealing region. The axial spacing of the sealing and support zones is substantially equal to the axial spacing of the sealing and support regions. Also, the outer diameter of the lateral support zone is slightly less than the inner diameter of the lateral support region such that as the sealing zone penetrates the sealing region, the support region receives the support zone and provides lateral support therefor which prevents transverse rocking of the pipette tip on the mounting shaft as might otherwise occur during touching off of the pipette tip and an accompanying undesired dislodging of the tip from the shaft.

Further, a preferred form of the LTS system includes the aforementioned controlled interference air tight fit and mating annular lateral support zone and region as well cooperative means on the pipette and pipette tip for limiting the axial travel of the tip on the mounting shaft. This insures uniform depth of mounting shaft penetration into the pipette tip to maintain uniform the desired tip interference with the mounting shaft as successive tips are mounted on and ejected from the mounting shaft and is to be distinguished from the pipette tip shoulder structure of previously mentioned U.S. Pat. No. 4,824,641.

Because of the above described cooperative structural features of the pipette tip and mounting shaft, the LTS system has proven to only require axial pipette tip mounting and ejection forces substantially equal to or less than one pound and to provide a stable air-tight seal of the tip on the shaft which is secure against undesired lateral rocking of the pipette tip on the mounting shaft. Thus, the LTS system requires a pipette user to generate so little hand and thumb force that repeated mounting and ejection of such pipette tips is unlikely to result in repetitive stress injury.

While the LTS system is in the process of revolutionizing the art of mounting and dispensing pipette tips in pipette devices, further development of the LTS system has revealed that similar functional benefits may be achieved with system modifications wherein the annular sealing surface for the LTS system comprises an outwardly directed annular seal located at a lower end of the pipette tip mounting shaft rather than comprising an inwardly projecting annular seal on the pipette tip. The present invention is directed to that newly discovered feature of the LTS system.

SUMMARY OF INVENTION

Accordingly, the present invention comprises a pipette tip and mounting shaft combination in an air displacement pipette wherein the pipette tip mounting shaft and pipette tip include axially spaced and mating annular sealing and substantially cylindrical lateral support zones and regions. The annular sealing zone comprises an annular sealing surface outward of the outer surface of the mounting shaft at a lower end thereof and the sidewall of the pipette tip in the sealing region is sufficiently thin that the sealing region will expand slightly and form an interference fit and air tight seal between the sealing surface and the sealing region when the sealing zone penetrates the sealing region. In one embodiment, the annular support zone on the mounting shaft may have an outer diameter slightly greater than an inner diameter of the annular support region on the pipette tip and a sidewall of the pipette tip in the annular support region may be sufficiently thin as to expand slightly to form an interference fit and even a secondary air tight seal between the mounting shaft and pipette tip when the support zone penetrates the support region.

BRIEF DESCRIPTION OF DRAWINGS

FIG. 3 is an enlarged fragmentary side view of an upper portion of the pipette tip and mounting shaft system of FIG. 2 showing the fluid tight seal between the sealing region and sealing zone, the mating relationship of the lateral support region and zone and a preferred embodiment of the cooperative means including a shoulder on the pipette tip for limiting mounting shaft penetration into the tip.

FIG. 4 is an enlarged fragmentary section side view of the sealing surface of the sealing zone of the pipette tip mounting within the circle 4 for the system of FIG. 3.

DETAILED DESCRIPTION OF INVENTION

Figure 1:
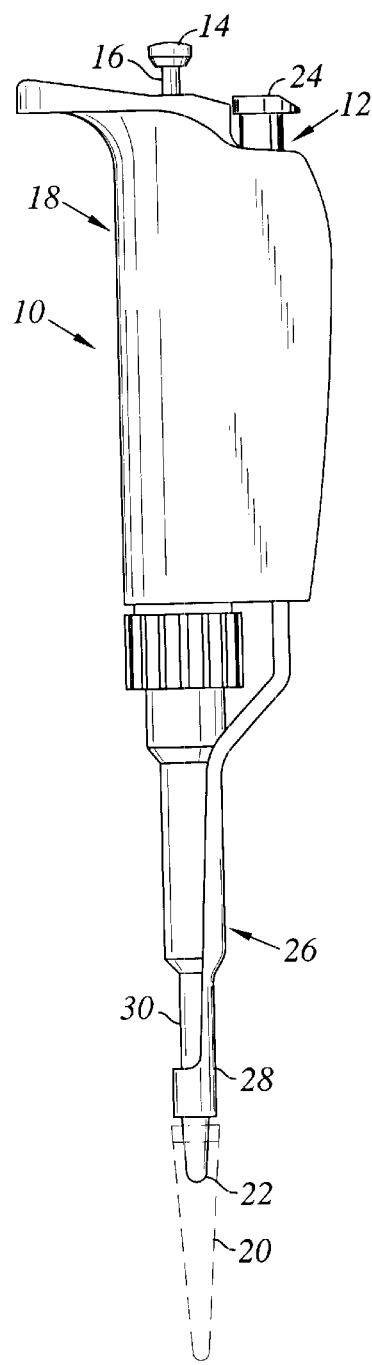
FIG. 1 is a side view of a standard manual pipette having a pipette tip mounted on a mounting shaft adjacent a lower end of a tip ejector mechanism of the pipette.

FIG. 1 illustrates a standard manual pipette resembling the PIPETMAN pipette sold exclusively in the United States by the Rainin Instrument Co. Inc., assignee of the present invention. The manual pipette is designated in FIG. 1 by the number 10 and includes a pipette tip ejector mechanism 12 described in U.S. Pat. No. 3,991,617 issued Nov. 16, 1976, which is incorporated herein by this reference.

The pipette 10 comprises a push button 14 connected by a rod 16 to a piston (not shown) located in the body or housing 18 of the pipette. The push button 14 may be depressed by a user exerting a downward force on the push button to cause downward movement of the piston of the pipette. When the push button 14 is released, a quantity of liquid to be sampled is sucked into a disposable pipette tip 20 releasably secured to a lower end of a pipette tip mounting shaft 22 of the pipette. The sample then may be transferred into another vessel by once more exerting a downward force on the push button 14. After such use, it is common practice to eject the pipette tip 20 from the mounting shaft 22 and replace it with a new pipette tip for repeated operation of the pipette 10 in aspirating and dispensing a new sample fluid.

The pipette tip ejector mechanism 12 is employed to eject the tip 20 from the mounting shaft 22. In this respect, the mechanism 12 comprises a push button 24 connected to a rod located in a passage (not shown) provided in an upper part of the hand holdable housing 18 of the pipette 10. The passage and rod are arranged so as to be able to impart to the rod a movement of translation parallel to an axis of the pipette in opposition to a spring (not shown) normally urging the rod in an upward position. A removable tip ejector member or arm 26 including a tubular upper end extends from a lower end of the rod and from the rod follows the general exterior contour of the housing 18 of the pipette to terminate in a sleeve 28. The sleeve 28 encircles a conical lower end 30 of the pipette tip mounting shaft 22 which tightly receives the upper end of the disposable pipette tip 20. To eject the pipette tip 20 from the lower end of the mounting shaft 22, a user grips the pipette housing 18 and using his or her thumb presses downward on the push button 24. The downward force on the push button is translated by the rod to the tip ejector arm 26 and hence to the sleeve 28 which presses down on an upper end of the pipette tip. When the downward force transferred by the sleeve 28 exceeds the friction between the pipette tip 20 and the mounting shaft 22, the pipette tip is propelled from the mounting shaft. Upon a release of the push button 24, the spring returns the tip ejector mechanism 12 to its normal position with the sleeve spaced slightly from the upper end of a replacement pipette tip which is inserted onto the mounting shaft 22 readying the pipette 10 for its next aspiration and dispensing operation.

As previously stated, for standard small and moderate volume pipettes, the pipette tip mounting shaft 22 has an inward axial taper of between two and five degrees from the longitudinal axis of the mounting shaft. As also previously stated, standard small and moderate volume pipettes tips for use with such standard pipette tip mounting shafts include a relatively long frusto-conical annular sealing band or inner surface contiguous with the open proximal end of the tip for engaging and sealing with the frusto-conical distal end of the pipette tip mounting shaft to provide lateral stability for the tip on the shaft. The angle of taper of the sealing surface is usually within about one degree of the two to five degrees inward taper of the mounting shaft and the length of the sealing surface on the shaft is such that in forming the annular seal the tip is also fairly stable on the shaft. In forming the desired annular seal, the frusto conical annular sealing region along with the balance of the open proximal end of the pipette tip is required to stretch like a hoop outwardly normal to the mating sloping surface of the pipette tip mounting shaft. Because of the length of the sealing region and the relatively thick sidewall of the standard tip, large plastic forces are generated in the tip material which resist such outward hoop stretching and require exertion of large axial forces on the tip in order to mount the standard tip on the mounting shaft and create the necessary annular fluid tight seal. Often, axial forces between 8 and 15 pounds are required to mount a standard pipette tip on a standard mounting shaft and create the desired fluid tight seal. Such axial forces are generated by the hand and forearm of a pipette user in exerting a pipette tip mounting shaft into a pipette tip usually held in a pipette tip mounting rack. Of course, when it is desired to eject such a firmly mounted tip from a pipette tip mounting shaft, an axial force of approximately ten (10) pounds must be exerted on the upper edge of the pipette tip to overcome the friction forces between the pipette tip and shaft and to eject the tip from the shaft.

As previously described, the downward tip ejection forces are exerted by the pipette user pressing downward with his or her thumb on the top of the push button 24 to translate axial force through the ejector arm 26 to the top of the pipette tip 20. To eject the standard pipette tip from its associated mounting shaft requires the pipette user to generate an axial ejection force of about 10 pounds. Over the course of several repeated ejection operations, the thumb and hand of the user will become physically stressed. This often results in repetitive motion injury to the thumb and hand and in extreme cases carpal tunnel syndrome.

As previously indicated, the present invention provides a novel mounting shaft and pipette tip system which allows for the easy and firm mounting of the pipette tip of the present invention on its associated mounting shaft and the easy ejection of the pipette tip from the mounting shaft by the application of axial mounting and ejection forces of about one (1) pound.

Figure 2:
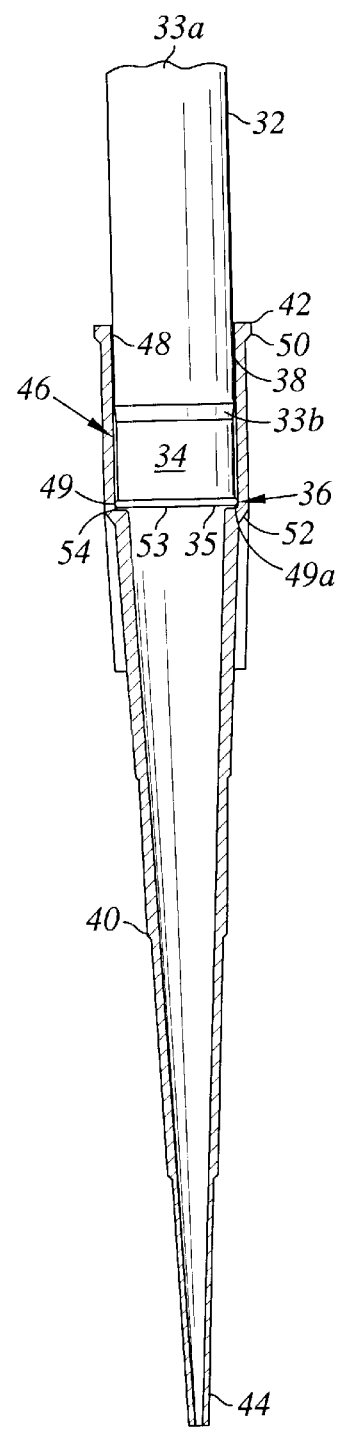
FIG. 2 is a cross sectional side view of one embodiment of the pipette tip and mounting shaft system of the present invention.

A preferred embodiment of the structure of the pipette tip and mounting shaft system of the present invention is depicted in FIG. 2 and shown in enlarged detail in FIG. 3. As there illustrated, the system comprises a pipette tip mounting shaft 32 and a pipette tip 40. The mounting shaft 32 preferably comprises an axially elongated body including an upper substantially cylindrical portion 33a and a substantially cylindrical lower distal end portion 34. The upper portion 33a is designed to extend vertically downward from an associated pipette, such as 10 in FIG. 1. In the illustrated version of the mounting shaft 32, the lower distal end portion 34 steps radially inward from the upper portion 33a at a transition 33b. As depicted in FIGS. 2 and 3, the outer surfaces of the upper and lower distal portions of the mounting shaft 32 preferably comprise annular or substantially cylindrical and axially spaced outer surface regions defining an annular sealing zone 36 at or immediately adjacent a lower end 35 of the distal end portion 34 and an annular lateral support zone 38 on the upper portion 33a adjacent the transition 33b of the shaft 32. The pipette tip 40 of the illustrated system is an elongated plastic tube comprising an open proximal end 42 and an open conical distal end 44. Like the mounting shaft 32, the pipette tip 40 also comprises annular or substantially cylindrical and axially spaced inner surface regions defining an annular sealing region 46 and an annular lateral support region 48 for mating with the sealing and support zones 36 and 38 respectively, on the mounting shaft. As used herein, "substantially cylindrical" means an annular surface having an axial taper of one and one-half degrees or less.

FIG. 4 illustrates in enlarged detail a preferred embodiment of the sealing zone 36 and comprises the portion of the pipette tip mounting shaft 32 of FIG. 3 within the circle 4. As shown, the sealing zone 36 comprises a lower end portion of the distal end 34 of the mounting shaft 32 and includes an annular radially extending outward extension 49 adjacent the lower end 35 of the mounting shaft. The outermost surface of the extension 49 forms a very narrow annular sealing surface 49a outward of the mounting shaft for engaging the annular sealing region 46 of the pipette tip 40 to form the previously described air-tight seal between the tip and mounting shaft. In the embodiment of the mounting shaft illustrated in FIGS. 3 and 4 the sealing surface 49a is outwardly rounded to define a very narrow annular sealing band or curved sealing edge for engaging and creating the fluid tight seal with the smooth substantially cylindrical inner surface of the sealing region 46 of the pipette tip 40. In use, relatively small pipette tip mounting and ejection forces are associated with this structural configuration.

Figure 5:
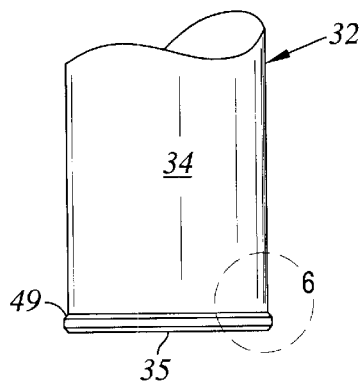
FIG. 5 is an enlarged fragmentary side view of a distal end portion of a second embodiment of a pipette tip mounting shaft for the system of the present invention.
Figure 6:
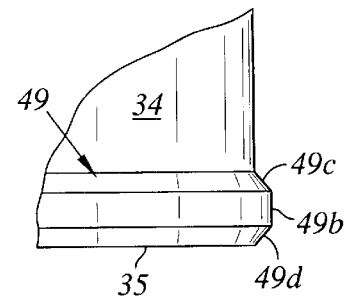
FIG. 6 is an enlarged fragmentary side view of the sealing surface of the sealing zone of the pipette tip mounting shaft within the circle 6 in FIG. 5.

Alternate structures for the sealing surface 49a having such different shapes and dimensions are shown in FIGS. 5–10. In FIGS. 5 and 6, the annular extension 49 at the lower end of the distal end portion 34 includes an outermost annular substantially cylindrical section 49b defining the sealing surface 49a for this embodiment. As illustrated, the extension 49 also includes inwardly flaring annular sections 49c and 49d between the section 49b and the outer surface of the distal end portion 34 and bottom surface 35 respectively. In use, the mounting an ejection forces associated with this structural configuration are slightly greater than those associated with the configuration of FIGS. 3 and 4 due to the broader sealing surface and the edge configurations thereof.

Figure 7:
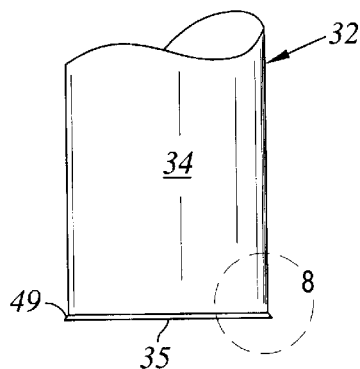
FIG. 7 is an enlarged fragmentary side view of a distal end portion of a third embodiment of a pipette tip mounting shaft for the system of the present invention.
Figure 8:
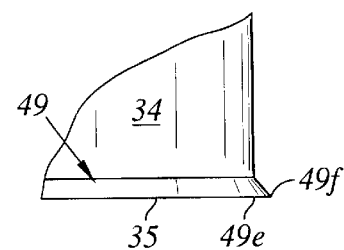
FIG. 8 is an enlarged fragmentary side view of a sealing surface of the sealing zone of the pipette tip mounting shaft within the circle 8 in FIG. 7.

In FIGS. 7 and 8, the annular extension 49 comprises a downwardly and outwardly flaring section 49e between the outer surface of the section 34 and the bottom surface 35. The outermost edge 49f of the section 49e defines the sealing surface or line seal 49a for this embodiment. Because of the relatively sharp edge seal included in this structural configuration, the associated tip mounting and ejection forces are respectively somewhat greater and somewhat less than those associated with the structural configurations of FIGS. 5 and 6. This type of sealing surface configuration has been observed as occurring naturally in some of applicants molded shafts due to plastic shrinkage combined with changes in internal cross-section.

Figure 9:
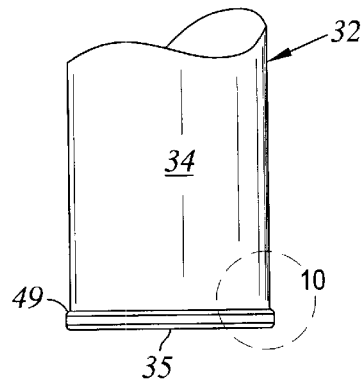
FIG. 9 is an enlarged fragmentary side view of a distal end portion of a fourth embodiment of a pipette tip mounting shaft for the system of the present invention.
Figure 10:
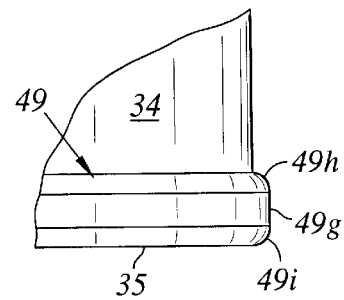
FIG. 10 is an enlarged fragmentary side view of a sealing surface of the sealing zone of the pipette tip mounting shaft within the circle 10 in FIG. 9.

In FIGS. 9 and 10, the annular extension 49 at the lower end of the distal end portion 34 includes an outermost annular substantially cylindrical section 49g defining the sealing surface 49a for this embodiment. As illustrated, the extension also includes concave curved annular sections 49h and 49i between the section 49g and the outer surface of the distal end portion 34 and bottom surface 35 respectively. In use, the mounting and ejection forces of this configuration are less than those associated with the structure configuration of FIGS. 5 and 6 due to the rounded nature of the sections 49h and 49i.

As illustrated in FIGS. 2 and 3, the outer diameter of the extension 49 including the annular sealing surface 49a is slightly greater than the inner diameter of the annular sealing region 46 on the inner surface of the pipette tip 40. This applies for each of the embodiments of the sealing surfaces illustrated in FIGS. 5–10. Also, the sidewall 50 of the tip in the area of the annular sealing region 46 is sufficiently thin that the annular sealing region expands slightly to form an interference fit and air tight seal between the mounting shaft 32 and the pipette tip 40 when the sealing zone 36 penetrates the sealing region 46. In practice, it has been found that the desired interference fit is formed when the difference in the outer diameter of the annular sealing zone and the inner diameter of the annular sealing region is at least 0.05 millimeters (mm). Further, it has been found that in practice that the wall thickness of the pipette tip in the area of the sealing region 46 is preferably between 0.20 and 0.50 mm.

As illustrated in FIGS. 2 and 3, the axial spacing of the sealing and support zones (36,38) on the mounting shaft 32 is substantially equal to the axial spacing of the sealing and support regions (46,48) on the pipette tip 40. Also, the outer diameter of the lateral support zone 38 is slightly less than the inner diameter of the lateral support region 48 such that as the sealing zone 36 penetrates the sealing region 46, the support region 48 receives the support zone 38 and provides lateral support therefor which prevents transverse rocking of the pipette tip 40 on the mounting shaft 32 as might otherwise occur during "touching off" of the pipette tip and an accompanying undesired dislodging of the tip from the shaft. In these regards, it is preferred that the axial spacing of the mating lateral support zone 38 and region 48 from the sealing zone and region 36,46 is substantially equal to the inner diameter of the pipette tip 40 in the support region. Such a length relationship provides excellent lateral stability for the pipette tip 40 on the mounting shaft 32.

Further, as illustrated in FIGS. 2 and 3, the present invention includes cooperative means 52 on the pipette of the present invention and the pipette tip 40 for limiting the axial travel of the tip on the mounting shaft 32. This insures uniform depth of mounting shaft penetration into the pipette tip to maintain uniform tip interference with the mounting shaft as successive tips are mounted on and ejected from the mounting shaft. In the embodiment illustrated in FIGS. 2 and 3, such cooperative means 52 comprises an annular, upwardly facing, inwardly directed shoulder 53 on the inner surface of the pipette tip 40 immediately adjacent the sealing region 46. The shoulder 53 is designed such that an upper surface thereof engages a downwardly facing surface such as the bottom 35 of the distal end 34 of the mounting shaft 32 at an outer circumferential portion thereof.

Figure 12:
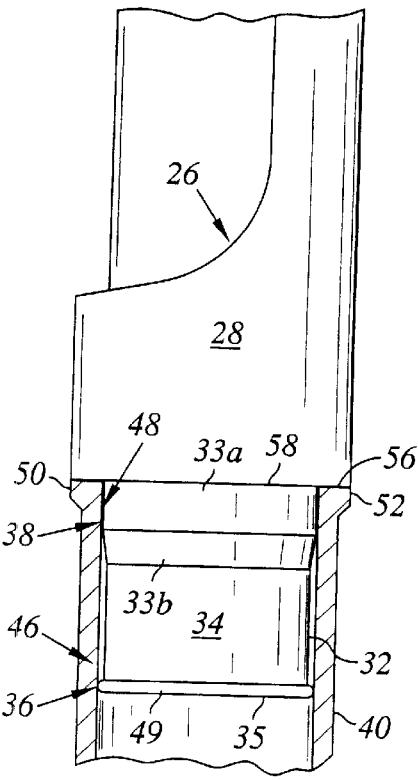
FIG. 12 is an enlarged sectional side view similar to FIG. 3 in addition showing an alternative embodiment of the cooperative means including a lower end of the pipette tip ejector of a pipette for limiting mounting shaft penetration into the tip.
Figure 13:
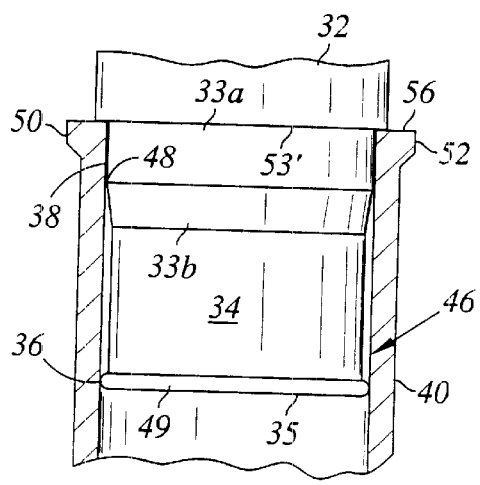
FIG. 13 is an enlarged fragmentary side view similar to FIG. 3 in addition showing a second alternative embodiment of the cooperative means including a shoulder on the pipette tip mounting shaft for limiting mounting shaft penetration into the tip.

Alternate embodiments of the cooperative means 52 are depicted in FIG. 12 and FIG. 13. In FIG. 13, the cooperative means 52 comprises an outwardly directed downwardly facing annular shoulder 53' on the upper portion 33a of the pipette tip mounting shaft 32 which upon insertion of the shaft into the open proximal 42 of the tip engages the upper annular edge 56 of the tip to halt further penetration of the shaft into the tip. In FIG. 12, the cooperative means 52 is depicted as comprising a bottom 58 of the sleeve 28 of the pipette tip ejector mechanism 26 illustrated and described with respect to FIG. 1. When the bottom surface 58 engages the upper annular edge 56 of the pipette tip 40, further penetration of the mounting shaft 32 into the pipette is halted.

Also, FIGS. 12 and 13 illustrate embodiments of the present invention where the outer diameter of the pipette tip mounting shaft 32 in the lateral support zone 38 is equal to or slightly greater than the inner diameter of the pipette tip 40 in the lateral support region 48. In such structures there is an interference fit between the lateral support zone and region. By proper dimensioning of the outer diameter of the lateral support zone relative to the lateral support region, a secondary fluid-tight seal may be formed between the mounting shaft 32 and the pipette tip 40, if desired.

Figure 11:
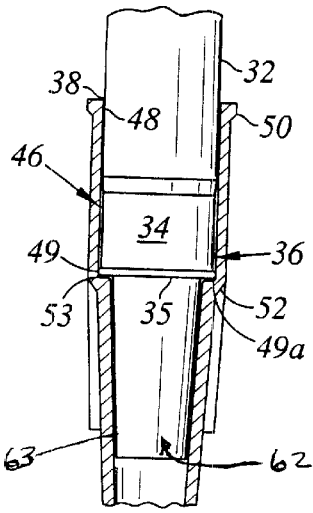
FIG. 11 is a cross sectional side view of an alternative embodiment of the pipette tip and mounting shaft system of the present invention including a mounting shaft extension for reducing air volume effects associated with air displacement pipettes.

While in the foregoing, particular preferred embodiments of the pipette tip of the present invention have been described and illustrated in detail, changes and modifications may be made without departing from the spirit of the present invention. For example, FIG. 11 depicts an alternate embodiment of the present invention which include the cooperative means 52 as depicted in FIGS. 2 and 3. In addition to the structure of FIGS. 2 and 3, the embodiment of FIG. 11 includes an elongated substantially cylindrical extension 62 from the bottom of the distal end portion 34 of the mounting shaft 32. The extension 62 is coaxial with the mounting shaft and includes an outer sidewall 63 spaced from the inner surface of the pipette tip 40. The extension 62 functions to decrease the air volume captured in the pipette of the present invention and reduces the air volume effects commonly associated with air displacement pipettes.

Accordingly the present invention is to be limited in scope only by the following claims.

What is claimed is:

1. An air displacement pipette comprising a pipette tip mounting shaft and a pipette tip including axially spaced and mating annular sealing and substantially cylindrical lateral support zones and regions, respectively the annular sealing zone comprising an annular sealing surface outward of an outer surface of the mounting shaft at a lower end thereof and a sidewall of the pipette tip in the sealing region being sufficiently thin as to expand slightly and form an interference fit and air tight seal between the sealing surface and the sealing region when the sealing zone penetrates the sealing region.

2. The pipette of claim 1 wherein the sealing surface is an outermost surface of an annular radially extending outward extension adjacent a lower end of the mounting shaft.

3. The pipette of claim 2 wherein the sealing surface is outwardly rounded to define a narrow sealing band or edge.

4. The pipette of claim 2 wherein the sealing surface comprises an substantially cylindrical section with inwardly flaring annular sections between a top of the substantially cylindrical section and the outer surface of the mounting shaft and between a bottom of the substantially cylindrical section and the bottom of the mounting shaft.

5. The pipette of claim 2 wherein the sealing surface comprises an substantially cylindrical section with concave curved annular sections between a top of the substantially cylindrical section and the outer surface of the mounting shaft and between a bottom of the substantially cylindrical section and the bottom of the mounting shaft.

6. The pipette of claim 2 wherein the sealing surface comprises an annular downwardly and outwardly flaring section between an outer edge surface and bottom of the mounting shaft.

7. In an air displacement pipette, the combination comprising:
   a pipette tip mounting shaft comprising an axially elongated body including a distal end and annular or substantially cylindrical and axially spaced outer surface regions defining an annular sealing zone and an annular lateral support zone, the sealing zone comprising an annular sealing surface outward of an outer surface of the mounting shaft at a lower end thereof; and
   a pipette tip comprising an elongated tube comprising an open proximal end, an open conical distal end and annular or substantially cylindrical and axially spaced inner surface regions defining an annular sealing region and an annular lateral support region for mating with the sealing zone and region respectively, a sidewall of the pipette tip in the sealing region being sufficiently thin as to expand slightly and form an interference fit and air tight seal between the sealing surface and the sealing region when the sealing zone penetrates the sealing region.

8. The combination of claim 7 wherein the annular sealing zone on the mounting shaft has an outer diameter slightly greater than an inner diameter of the annular sealing region on the pipette tip.

9. A pipette tip mounting shaft comprising an axially elongated body including a distal end and annular or substantially cylindrical and axially spaced outer surface regions defining an annular sealing zone and an annular lateral support zone for mating with annular or substantially cylindrical and axially spaced inner surface regions defining an annular sealing region and an annular lateral support region for a pipette tip, the sealing zone comprising an annular sealing surface outward of an outer surface of the mounting shaft at a lower end thereof and having an outer diameter slightly greater than the inner diameter of the sealing region of the pipette tip wherein the sidewall thereof is sufficiently thin as to expand slightly and form an interference fit and air tight seal when the sealing zone penetrates the sealing region.

10. The pipette tip mounting shaft of claim 9 wherein the sealing surface is an outermost surface of an annular radially extending outward extension adjacent a lower end of the mounting shaft.

11. The pipette tip mounting shaft of claim 10 wherein the sealing surface is outwardly rounded to define a narrow sealing band or edge.

12. The pipette mounting shaft of claim 10 wherein the sealing surface comprises an substantially cylindrical section with inwardly flaring annular sections between a top of the substantially cylindrical section and the outer surface of the shaft and between a bottom of the substantially cylindrical section and the bottom of the mounting shaft.

13. The pipette mounting shaft of claim 10 wherein the sealing surface comprises an substantially cylindrical section with concave curved annular sections between a top of the substantially cylindrical section and the outer surface of the shaft and between a bottom of the substantially cylindrical section and the bottom of the mounting shaft.

14. The pipette tip mounting shaft of claim 10 wherein the sealing surface comprises an annular downwardly and outwardly flaring section between an outer edge surface and bottom of the mounting shaft.

* * * * *